(12) United States Patent
Sullivan et al.

(10) Patent No.: US 6,187,038 B1
(45) Date of Patent: Feb. 13, 2001

(54) SMALL BORE BIOLOGIC GRAFT WITH THERAPEUTIC DELIVERY SYSTEM

(75) Inventors: Steven G. Sullivan, Austin, TX (US); Donald E. Chickering, Framingham, MA (US); John P. Ranieri, Austin, TX (US)

(73) Assignee: Sulzer Carbomedics Inc., Austin, TX (US)

(*) Notice: Under 35 U.S.C. 154(b), the term of this patent shall be extended for 0 days.

(21) Appl. No.: 09/056,956

(22) Filed: Apr. 8, 1998

(51) Int. Cl.[7] .................................................. A61F 2/00
(52) U.S. Cl. ....................... 623/1.43; 623/1.27; 623/1.42
(58) Field of Search ................................ 623/1, 12, 1.27, 623/1.42, 1.43

(56) References Cited

U.S. PATENT DOCUMENTS

| | | | |
|---|---|---|---|
| 4,193,138 | 3/1980 | Okita | 3/1.4 |
| 4,441,215 | 4/1984 | Kaster | 3/1.4 |
| 4,743,251 * | 5/1988 | Barra | 623/1 |
| 4,929,602 | 5/1990 | Harker et al. | 514/18 |
| 4,994,071 * | 2/1991 | MacGregor | 623/1 |
| 5,123,917 * | 6/1992 | Lee | 623/1 |
| 5,147,514 | 9/1992 | Mechanic | 204/157 |
| 5,152,782 * | 10/1992 | Kowligi | 623/1 |
| 5,197,977 | 3/1993 | Hoffman, Jr. et al. | 623/1 |
| 5,332,475 | 7/1994 | Mechanic | 204/157 |
| 5,383,928 | 1/1995 | Scott et al. | 623/1 |
| 5,455,039 | 10/1995 | Edelman et al. | 424/422 |
| 5,540,928 | 7/1996 | Edelman et al. | 424/422 |
| 5,628,781 | 5/1997 | Williams et al. | 623/1 |
| 5,667,523 * | 9/1997 | Bynon | 606/198 |
| 5,700,286 | 12/1997 | Tartaglia et al. | 623/1 |

* cited by examiner

*Primary Examiner*—Michael J. Milano
(74) *Attorney, Agent, or Firm*—Timothy L. Scott; Kenneth S. Barrow

(57) ABSTRACT

A composite graft for a fluid-carrying vessel in a living body, comprising: an inner vessel comprising a biologic collagenic material that has been stabilized, an outer member surrounding at least a segment of the inner vessel and defining an annulus between the inner vessel and the sleeve, the outer member comprising a polymeric fabric, and a bioactive compound in said annulus, said bioactive compound being carried on a time-release vehicle. The bioactive compound is preferably an occlusion-preventing agent. Alternatively, the sleeve includes the bioactive compound, either on its inner surface or integrally as part of its fibers.

32 Claims, 2 Drawing Sheets

SMALL BORE BIOLOGIC GRAFT WITH THERAPEUTIC DELIVERY SYSTEM

FIELD OF THE INVENTION

The present invention relates to a graft capable of replacing a blocked, occluded or damaged portion of a small diameter artery and more particularly, to a small bore biologic graft with a therapeutic drug delivery system that give it an improved resistance to occlusion by platelets, thrombi or smooth muscle cell proliferation. Still more particularly, the present invention relates to a two-part graft comprising an inner vessel and an outer sleeve and a drug delivery composition in the annulus therebetween.

BACKGROUND OF THE INVENTION

Coronary artery bypass graft (CABG) surgery is a surgical procedure intended to restore blood flow to ischemic heart muscle whose blood supply has been compromised by occlusion or stenosis of one or more of the coronary arteries. One method for performing CABG surgery entails using a length of graft material to bypass the blockage or narrowing. The graft is typically an autologous graft, such as a portion of the saphenous vein or internal mammary artery, or a synthetic graft, such as one made of Dacron or Gore-Tex tubing.

Atherosclerosis is the major disease that affects the blood vessels. This disease may have its beginnings early in life and is first noted as a thickening of the arterial walls. This thickening is an accumulation of fat, fibrin, cellular debris and calcium. The resultant narrowing of the lumen of the vessel is called stenosis. Vessel stenosis impedes and reduces blood flow. Hypertension and dysfunction of the organ or area of the body that suffers the impaired blood flow can result. As the buildup on the inner wall of a vessel thickens, the vessel wall loses the ability to expand and contract. Also, the vessel loses its viability and becomes weakened and susceptible to bulging, also known as aneurysm. In the presence of hypertension or elevated blood pressure, aneurysms will frequently dissect and ultimately rupture.

Small vessels, such as the arteries that supply blood to the heart, legs, intestines and other areas of the body, are particularly susceptible to atherosclerotic narrowing. When an artery in the leg or intestine is affected, the resultant loss of blood supply to the leg or segment of the intestine may result in gangrene. Atherosclerotic narrowing of one or more of the coronary arteries limits and in some instances prevents blood flow to portions of the heart muscle. Depending upon the severity of the occlusion and its location within the coronary circulation system, pain, cardiac dysfunction or death may result.

It is preferable to correct aneurysms and stenosis of major arteries using plastic reconstruction that does not require any synthetic graft or patch materials. However, if the disease is extensive and the vessel is no longer reliable, the blocked or weakened portion is usually replaced with a graft. In such case, the involved vessel section is transected and removed and a synthetic patch, conduit or graft is sewn into place.

Patients with coronary artery disease, in which blood flow to part of the heart muscle has been compromised, receive significant benefit from CABG surgery. Because the coronary arteries are relatively small, CABG surgery requires the use of small diameter grafts, typically less than 3–5 mm in diameter. Because they cause more problems than biologic grafts, as discussed below, synthetic grafts are used in CABG surgery only on infrequent occasions. Thus, in a patient who undergoes coronary artery bypass surgery, a non-critical artery or vein of small diameter is harvested from elsewhere in the body and sewn into place in a manner that reestablishes flow to the area of the heart that earlier lost its blood supply because of atherosclerotic blockage. This is referred to as an autograft. When no suitable artery or vein can be harvested from the patient, an allograft (from the same species) or xenograft (from another species) vessel may be employed. However, experience with allografts and xenografts is limited and not typically satisfactory.

In CABG cases where an autograft is available, the saphenous vein (SV) in the leg and the internal mammary artery (IMA) are the vessels most commonly harvested for use as a bypass graft. It has been found that most saphenous vein bypass grafts, in time, exhibit a narrowing of the lumen that is different from atherosclerosis. It is believed this is a pathologic response of the vein because it is of different cellular construction and composition than an artery, thus making it unsuitable for use as an artery. Current estimates of the life expectancy of saphenous vein bypass grafts do not exceed 7 years. In addition, harvesting a saphenous vein autograft is a tedious surgical task and not always rewarded with the best quality graft. Further, removal of the saphenous vein disrupts the natural venous blood return from the leg and is not therapeutically recommended except for certain cases, such as in a patient with advanced venous disease. Finally, harvesting an autograft in the operating room requires additional surgical time and expense.

While the patency rate is better when the internal mammary artery is used, use of the internal mammary artery as autograft material may lead to sternal nonunion and mediastinitis. Furthermore, if multiple bypasses are indicated, the internal mammary artery may not provide sufficient graft material.

Hence, there is a desire to provide a small bore synthetic graft material for coronary artery bypass. Clinical experience with small diameter synthetic grafts for coronary artery bypass dates back to the mid 1970's, with limited success. When a synthetic vascular prosthesis (graft) is implanted, the fine pores of the vessel are clogged by clotted blood, and the inside surface of the vessel is covered by a layer of the clotted blood. The clotted blood layer is composed largely of fibrin, and the thickness of the fibrin layer varies, depending on the material and surface structure of the blood vessel. When a knitted or woven fabric such as polyester or polytetrafluoroethylene (PTFE) is used, the fibrin thickness typically approaches about 0.5 to about 1 mm. Also, overproliferation of smooth muscle cells (SMC) as part of the natural repair process may contribute to luminal occlusion. Despite the different methods and techniques of graft construction however, such as woven or knit, velour, texturized or nontexturized, tight or loose, fine or coarse, expanded or non-expanded, variations in fiber diameter and wall thickness, etc., no graft of small lumen diameter has shown a satisfactory resistance to blockage resulting from fibrin deposition and cellular adhesion. It is believed that the tendency of synthetic grafts to become occluded is due in part to the thrombogenic nature of the nude, i.e., nonendothelialized, surface of the implanted prostheses. Furthermore, in instances where the vessel, and hence the replacement graft, are of small diameter, handling and surgical placement of the graft is difficult. Thus, the internal diameter may be compromised due either to surgical technique or biological response. In some cases, the graft may become entirely occluded shortly after surgery.

Accordingly, synthetic vascular grafts are successful only with blood vessels having a large enough inside diameter that occlusion due to cell growth on the inner surface does not occur. This typically requires arteries having an inside diameter of 5 to 6 mm or more. Generally, vascular prostheses made of woven or knitted fabrics are not successful when the inside diameter is less than approximately 5 mm, and particularly not when the inside diameter is less than 4 mm.

Hence, it is desired to provide a small bore biologic graft that resists blocking due to fibrin deposition and cellular adhesion. The desired graft must be readily available, easily manipulated by the surgeon and effective at containing blood flowing through it.

BRIEF SUMMARY OF THE INVENTION

The present invention is a synthetic vascular graft that is particularly suited for use in small bore applications. The graft of the present invention comprises a biologic graft vessel comprising cross-linked collagen, surrounded by a structural sleeve comprising synthetic fiber. According to the present invention, an amount of an occlusion-preventing agent is positioned in the annulus between the graft and the sleeve. The occlusion-preventing agent preferably comprises a drug or combination of drugs that reduce thrombosis, help prevent intimal hyperplasia and help prevent smooth muscle cell proliferation. The occlusion-preventing agent is preferably carried in a time-release vehicle. The time-release vehicle is adjacent the outer surface of the biologic vessel and can be carried in either a viscous carrier medium, on a sleeve coating, or forming part of the sleeve material itself.

The components of the present graft are implanted sequentially in a series of steps that produce the fully assembled graft. After one end of the biologic graft vessel is attached to the first bypass point, the sleeve is placed over it and the second end of the biologic graft vessel is attached to the second bypass point. Both ends of the structural sleeve are sutured to the organ supporting the graft adjacent the anastomoses of the biologic graft vessel. The mixture containing the bioactive compound(s) is provided in a time-release mechanism, such as polymeric microspheres, and is injected through the sleeve into the annulus between the sleeve and the vessel.

BRIEF DESCRIPTION OF THE DRAWINGS

For a more detailed description of the present invention, reference will now be made to the accompanying Figures, wherein.

DETAILED DESCRIPTION OF THE PREFERRED EMBODIMENTS

Figure 1:
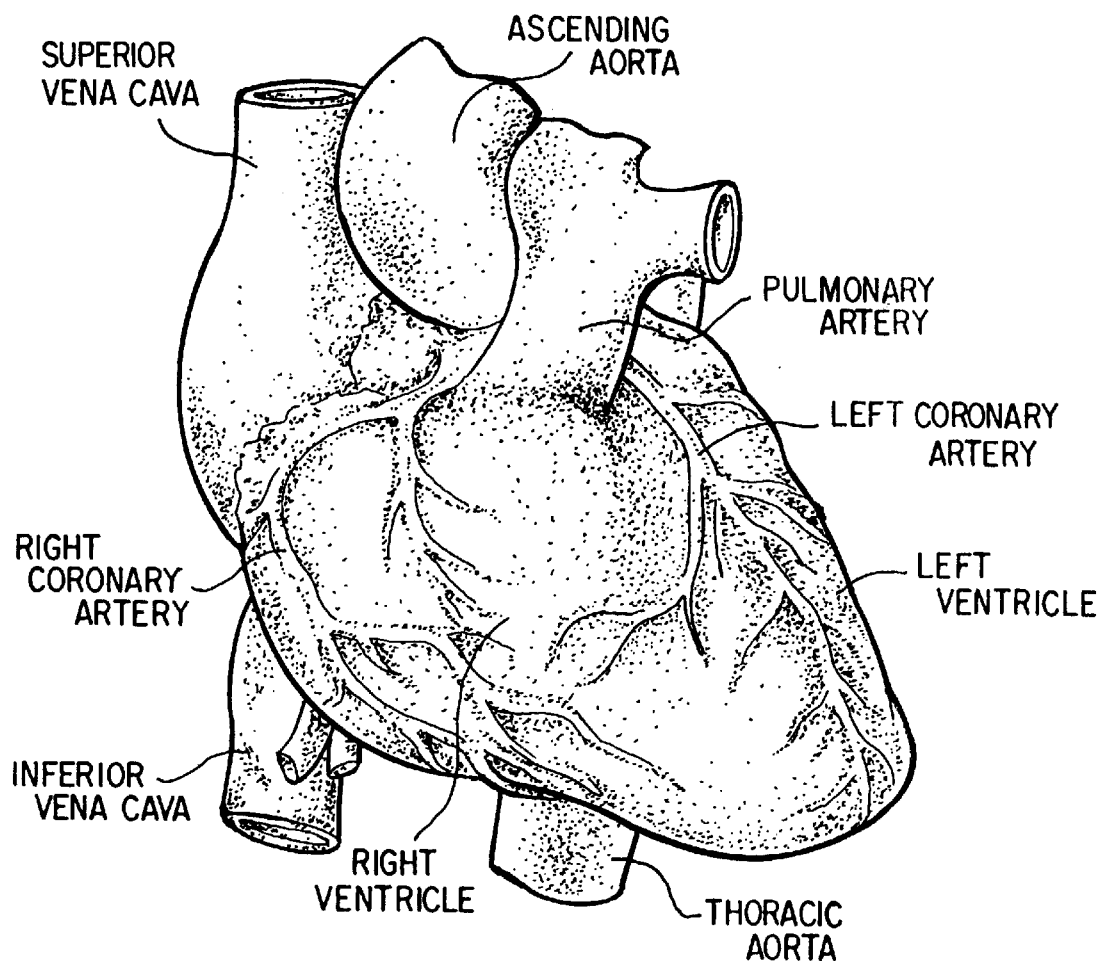
FIG. 1 is a drawing of a human heart showing the relative sizes of the various arteries.

Referring initially to FIG. 1, it can be seen that the coronary arteries are relatively small in size and lie along the surface of the heart. The coronary arteries provide the heart muscle with oxygen and nutrients. Thus, any occlusion or dysfunction of the coronary arteries can detrimentally affect the functioning of the heart. Depending upon the severity of the occlusion and its location within the coronary circulation system, pain, cardiac dysfunction or death may result.

Figure 2:
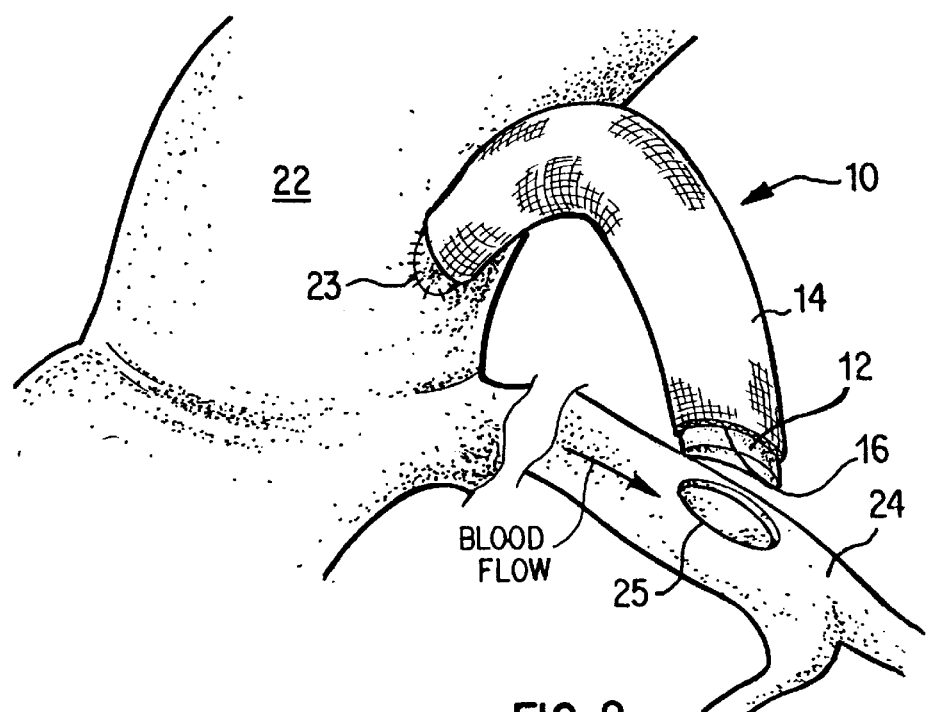
FIG. 2 shows the biologic graft vessel and the sleeve of the present invention, prior to anastomosis of the second end of the vessel to the bypassed vessel.

Referring now to FIG. 2, a small bore composite graft 10 constructed in accordance with the present invention comprises an inner vascular graft 12, around which is an outer sleeve 14. Between vascular graft 10 and sleeve 14 is a narrow annulus 16, which is filled with a bioactive compound following anastomosis, according to a preferred embodiment described below. According to the present invention, the bioactive compound is preferably carried in a timerelease vehicle, and can, in various embodiments, be coated on the inside of the sleeve or incorporated into the sleeve material itself.

According to a preferred embodiment, vascular graft 12 comprises a crosslinked, non-synthetic collagenic vessel. An example of a preferred vascular graft 12 is an ovine carotid artery that has been stabilized so as to resist enzymatic degradation following implantation. Vessels having any suitable diameter can be used, however, the present technique is particularly advantageous in that it eliminates the problems typically associated with very small diameter grafts, such as those having diameters less than 5 mm, and more particularly less than 4 mm.

According to a preferred technique, cross-linked, biologic, collagenic vessels are prepared using the following steps: a vessel is harvested, collected into neutral buffer, dissected from adjacent tissue, dipped in a high osmolarity (HO) solution so as to remove the cellular contents by osmotic pressure, placed in an HO solution with a photoreactive catalyst, and exposed to light from a light source while being washed with a solution of photoreactive catalyst. The exposure to light is preferably carried out at reduced temperature (10° C.) and preferably lasts about two days. Following treatment in this manner, the vessel is preferably placed in a de-staining solution (50% EtOH). This series of steps causes the collagen to become cross-linked and chemically modified. Collagen that is prepared in this manner is stabilized against enzymatic degradation and thus is better suited for implantation in living body. A more detailed discussion of the photofixing process can be found in U.S. Pat. Nos. 5,147,514 and 5,332,475, which are incorporated herein by reference in their entireties. While other techniques for cross-linking and chemically modifying collagen are known, photofixing is preferred because it renders the collagen sufficiently resistant to degradation by the host, without increasing the stiffness of the tissue to an unacceptable level.

Following the stabilization process; if the tissue is vascular, its branches are sutured shut, and it is leak tested, packaged and sterilized. For CAB surgery, the preferred graft will have an inside diameter of approximately 3–5 mm and a length of at least approximately 15 cm. Other possible sources for vascular graft 12 include the carotid artery of ostriches and cows. In addition, it will be understood by those skilled in the art that other sources of collagenic tissue can be used. For example, the bovine or porcine pericardium can be stabilized in the manner described above, formed into a tubular vessel and used as vascular graft 12.

Sleeve 14 preferably comprises a knitted, ribbed polyester sleeve having an inside diameter slightly larger than the outside diameter of vascular graft 12, such as are generally commercially available. For the preferred vessel described above the sleeve has an inside diameter of approximately 6–8 mm. The preferred sleeve is a knitted, ribbed polyester material having a pore size smaller than the diameter of the desired microspheres (described below). Material having the desired characteristics is available from Sulzer Vascutek, of Renfrewshire, Scotland. It will be understood that other materials and configurations for sleeve 14, both synthetic and of natural origin, can be used in place of the knitted, ribbed polyester sleeve and are within the scope of the invention.

The graft 10 of the present invention further includes an amount of a bioactive compound(s) contained in a time-release mechanism. The bioactive compound may be a compound having any desired bioactivity, including antithrombotic, antibiotic, and/or antiproliferative properties. The time-release mechanism may be of any type sufficient to slowly release the bioactive compound(s), such as the ethylene vinyl acetate system described in Edelman et al., "Effect of controlled adventitial heparin delivery on smooth muscle cell proliferation following endothelial injury", Vol. 87, pp. 3773–3777, May 1990. In one preferred embodiment, the bioactive compound is mixed into a resorbable polymer, which is formed into microspheres. The microspheres in turn are carried in a carrier 30. Thus, an example of one preferred form of bioactive material comprises heparin-loaded poly lactic-co-glycolic acid 75:25 (PLGA) polymer microspheres having an average diameter of approximately between 0.5 $\mu$m and 2.5 $\mu$m. Heparin is both a potent anticoagulant and an inhibitor of smooth muscle cell proliferation. Other suitable occlusion-preventing agents, such as warfarin and protamine sulfate, could be used in place of heparin. Alternatively, separate drugs could be used to provide the desired anticoagulant and cell growth inhibitive properties. Identification of suitable occlusion-preventing agents is within the ability of those skilled in the art. Similarly, other resorbable polymers, such as poly-caprolactone, polydioxanone and polyanhydride could be used in place of the PLGA, so long as they are capable of retaining and gradually releasing the occlusion-preventing agent and do not interfere with its effectiveness.

One technique for forming the preferred heparin-loaded PLGA microspheres is spray drying. This entails dissolving the heparin in water, and dissolving the PLGA in a suitable solvent, such as ethyl formate. The heparin and PLGA solutions are then sonicated to emulsify them and pumped into a spray dryer. This produces microspheres of a suitable size. The microspheres loaded with heparin agent are preferably sterilized using any suitable conventional sterilization technique. Spray drying is preferred because the concentration of heparin in the microspheres can be controlled. Microspheres containing other bioactive agents can be formed in this manner, or by any other technique that produces the desired time-release effect. The period over which the bioactive compound is released from the time-release mechanism is preferably varied by varying the composition of the polymer in which the bioactive compound is dispersed.

The occlusion-preventing agent of the present invention need not be carried on microspheres, but can instead be carried on a time-release vehicle having any other suitable configuration including, but not limited to particles, film and fibers. Likewise, the time-release vehicle can be incorporated into the fiber(s) forming the sleeve itself.

A preferred fluid carrier for the microspheres preferably comprises a solution of polyvinylpyrrolidone (PVP) in water. The PVP solution effectively manages the static charge associated with dry PLGA microspheres. The carrier must be thin enough to allow it to flow into and fill annulus 16, yet viscous enough to be easily emplaced and to remain in the annulus during the suturing of opening 15. A slightly viscous carrier is also less likely to seep out of annulus 16 through the pores of the sleeve or any small opening that may remain between vascular graft 12 or sleeve 14 and the organ itself. PVP is used in one preferred embodiment because it is biologically inactive, successfully wets microspheres made of PLGA (necessary for dissolution of the heparin), does not dissolve the microspheres, and does not adversely affect the performance of the heparin. Other suitable carriers include, but are not limited to, solutions of glycerol and solutions of Pluronic®. The carrier is preferably steam sterilized.

When it is desired to replace a portion of a coronary artery or other vessel with the biologic graft of the present invention, the preferred microspheres are mixed with the preferred carrier and the vascular graft 12 is soaked in an anticoagulant solution prior to commencing the bypass surgery.

Figure 3:
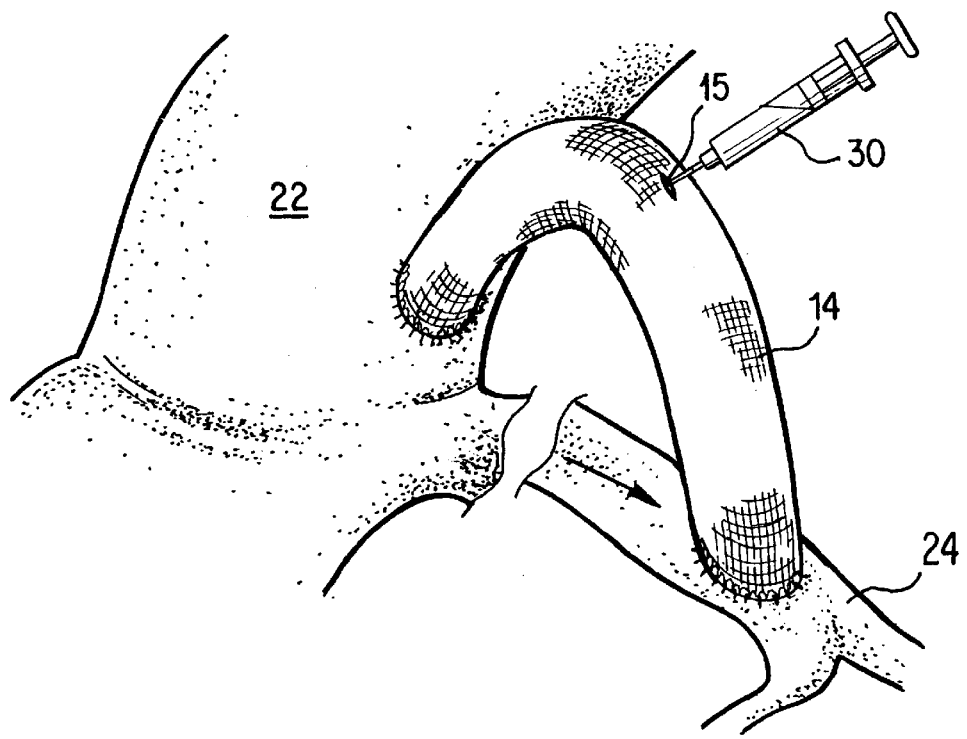
FIG. 3 shows the injection of the bioactive compound(s) into the sleeve of the present invention following attachment of the biologic graft vessel and the sleeve to the bypassed vessel.

One common CABG bypass technique involves using the graft material to bypass an occluded portion of a coronary artery as shown in FIGS. 2 and 3. This technique uses end-to-side anastomoses, in which the end of the graft is connected to the side of the host vessel(s). The steps for surgically implanting the small bore graft 10 of the present invention according to this technique are as follows:

a plug is removed from the host vessel(s) at each of the two bypass connection points 23, 25 (located on aorta 22 and a coronary artery 24, respectively, in this embodiment);

one end of the vascular graft 12 is sutured to the proximal bypass connection point 23; sleeve 14 is placed over the vascular graft 12;

the free end of vascular graft 12 is sutured to the distal bypass connection point 25;

the sleeve ends are sutured over the graft anastomoses; sleeve 14 is nicked as at 15 (FIG. 3);

a preselected amount of the microsphere/carrier mixture is injected into the space between the vascular graft and the sleeve, using a suitable injector 30; and the nick in the sleeve is sutured closed.

Another preferred technique includes the application of the bioactive compound (in a suitable time release mechanism) to the interior surface of the sleeve 14 prior to packaging of sleeve 14. An advantage of this technique is that the separate step of emplacing the bioactive compound in the annulus can be eliminated.

An alternative, similar technique (not illustrated) uses end-to-end anastomoses and includes removal of the bypassed portion of the original vessel.

EXAMPLE

In an illustrative procedure, the foregoing process and preferred components were used in a canine coronary lab bypass model. A mass of 0.8–1.0 grams per 10 cm of vascular graft length were used. The microspheres were PLGA 75:25 spray dried with 2–2.5 wt. % heparin. The vascular graft was soaked in 0.9% saline/10,000 U/ml heparin for 15 minutes prior to implantation. The microsphere/carrier mixture was injected using a 5 cc syringe. Three out of four grafts implanted according to this procedure had not failed or become inoperable due to occlusion after 270 days. It is believed that after approximately two months sufficient endothelialization has occurred at the anastomoses to inhibit thrombosis and SMC proliferation, even following depletion of the occlusion-preventing agent. The endothelial layer secretes nitrous oxide (NO) and prostacyclin, among other things.

The rate of release of the anti-coagulant and cell growth inhibitor was measured in vitro in a laboratory setup designed to simulate an in vivo application. Measurements taken in this apparatus showed that the composite graft described above released heparin in an initial burst of 15%, followed by approximately 1.5%/day for approximately 60 days.

By using a biologic graft vessel, the tendency of the graft to become occluded due to thrombosis and intimal hyperplasia is reduced. The sleeve of the present invention surrounds the biologic graft vessel and provides a means for maintaining an occlusion-preventing agent in the vicinity of the graft, which further reduces the tendency of the graft to become occluded. The occlusion-preventing agent in turn is released in a controlled manner over time through the vessel wall and further reduces the tendency of the vessel to occlude. The advantage of using the local modulator delivery of the present invention is that therapeutic levels of modulator can be maintained at the required site while keeping systemic levels nearly undetectable. The sleeve of the present invention further provides a mechanical support for the graft material, which can help prevent aneurysm.

While the present biologic graft has been described according to a preferred embodiment, it will be understood that departures can be made from some aspects of the foregoing description without departing from the scope of the invention. For example, the occlusion-preventing agent, the configuration of the drug delivery system, the polymer from which the time release vehicle is formed, the means for maintaining the occlusion preventing agent in the vicinity of the graft, the sleeve material, and the vessel material can all be varied, so long as the resultant graft is within the scope of the claims that follow. It is contemplated that stabilized ostrich carotid artery may be suitable for use as the biologic graft vessel, because of its length and relatively small diameter. Likewise, stabilized tissue from other sources is contemplated, including bovine and porcine pericardium. It is further contemplated that the bioactive compound can be affixed to the inner surface of the sleeve member, rather than carried in a fluid in the annulus. As such, the bioactive compound can be carried in resorbable microspheres, or in any other suitable vehicle, such as fiber, film or the like.

What is claimed is:

1. A composite graft for a fluid-carrying vessel in a living body, comprising:
   an inner vessel comprising a biologic material;
   an outer member surrounding at least a segment of said inner vessel and defining a space between said inner vessel and said outer member; and
   a bioactive compound in said space.

2. The graft according to claim 1 wherein said bioactive compound is an occlusion-preventing agent.

3. The graft according to claim 1 wherein said inner vessel comprises collagen.

4. The graft according to claim 1 wherein said inner vessel comprises a length of allogenic artery that has been stabilized.

5. The graft according to claim 1 wherein said inner vessel comprises a length of xenogenic artery that has been stabilized.

6. The graft according to claim 1 wherein said inner vessel comprises an ovine carotid artery that has been stabilized.

7. The graft according to claim 1 wherein said inner vessel comprises bovine or porcine pericardium that has been stabilized.

8. The graft according to claim 1 wherein said outer member is synthetic.

9. The graft according to claim 1 wherein said outer member comprises polymeric fibers.

10. The graft according to claim 1 wherein said outer member comprises polyester.

11. The graft according to claim 1 wherein said outer member comprises a knitted polymeric sleeve.

12. A composite graft for a fluid-carrying vessel in a living body, comprising:
    an inner vessel comprising a biologic material;
    an outer member surrounding at least a segment of said inner vessel and defining a space between said inner vessel and said outer member; and
    a bioactive compound in said space; wherein said bioactive compound comprises heparin.

13. A composite graft for a fluid-carrying vessel in a living body, comprising:
    an inner vessel comprising a biologic material;
    an outer member surrounding at least a segment of said inner vessel and defining a space between said inner vessel and said outer member; and
    a bioactive compound in said space;
    wherein said bioactive compound is carried on within resorbable polymeric microspheres.

14. The graft according to claim 13 wherein said microspheres are carried in a viscous liquid.

15. A composite graft for a fluid-carrying vessel in a living body, comprising:
    an inner vessel comprising a biologic material;
    an outer member surrounding at least a segment of said inner vessel and defining a space between said inner vessel and said outer member; and
    a bioactive compound in said space;
    wherein said bioactive compound is carried in a resorbable synthetic coating on an inner surface of said outer member.

16. The graft according to claim 1 wherein said bioactive compound is carried in a time-release vehicle.

17. A composite graft for a fluid-carrying vessel in a living body, comprising:
    an inner vessel comprising a biologic material;
    an outer member surrounding at least a segment of said inner vessel and defining a space between said inner vessel and said outer member; and
    a bioactive compound in said space:
    wherein said bioactive compound is carried in particles of PLGA.

18. A composite graft for a fluid-carrying vessel in a living body, comprising:
    an inner vessel comprising a biologic material; and
    an outer sleeve member surrounding at least a segment of said inner vessel, said outer sleeve member comprising a resorbable material including an occlusion-preventing agent.

19. A method for implanting a graft vascular prosthesis on a host organ, comprising the steps of:
    providing a first tubular component having first and second ends;
    connecting the first end of the first tubular component at a first bypass point on the host organ;
    providing a second tubular component having first and second ends and sliding it over the first tubular component so as to define an annulus between the first and second tubular components;
    connecting the second end of the first tubular component at a second bypass point on the host organ;

connecting the first and second ends of the second tubular component to the host organ; and including an occlusion-preventing agent in the annulus.

20. The graft according to claim 19 wherein the first tubular component comprises collagen.

21. The graft according to claim 19 wherein the first tubular component comprises xenogenic tissue that has been stabilized.

22. The graft according to claim 19 wherein the first tubular component comprises an ovine carotid artery.

23. The graft according to claim 19 wherein the second tubular component is synthetic.

24. The graft according to claim 19 wherein the second tubular component comprises polymeric fibers.

25. The graft according to claim 19 wherein the second tubular component comprises polyester.

26. The graft according to claim 19 wherein the second tubular component comprises a knitted polymeric sleeve.

27. The graft according to claim 19 wherein the occlusion-preventing agent comprises heparin.

28. The graft according to claim 19 wherein the occlusion-preventing agent is carried on resorbable polymeric microspheres.

29. The graft according to claim 28 wherein the microspheres are carried in a viscous liquid.

30. The graft according to claim 19 wherein the occlusion-preventing agent is carried in a time-release vehicle.

31. The graft according to claim 19 wherein the occlusion-preventing agent is carried in particles of PLGA.

32. A composite graft for a fluid-carrying vessel in a living body, comprising:

an inner vessel comprising a biologic collagenous material that has been stabilized; and an outer member surrounding at least a segment of said inner vessel and defining an annulus between said inner vessel and said outer member, said outer member comprising a polymeric fabric, and containing an occlusion-preventing agent carried in a time-release vehicle.

* * * * *